United States Patent
Gu et al.

(10) Patent No.: US 7,661,290 B2
(45) Date of Patent: Feb. 16, 2010

(54) GAS SENSOR TEST AND CALIBRATION SYSTEM

(75) Inventors: Yuandong Gu, Plymouth, MN (US); Peter Tobias, Minnetonka, MN (US); Alex L. Peterson, Platteville, WI (US); Wei Yang, Minnetonka, MN (US)

(73) Assignee: Honeywell International Inc., Morristown, NJ (US)

( * ) Notice: Subject to any disclaimer, the term of this patent is extended or adjusted under 35 U.S.C. 154(b) by 207 days.

(21) Appl. No.: 11/781,186

(22) Filed: Jul. 20, 2007

(65) Prior Publication Data

US 2009/0019913 A1   Jan. 22, 2009

(51) Int. Cl.
  *G12B 13/00*   (2006.01)
(52) U.S. Cl. .................. 73/1.03; 73/1.01; 73/1.02; 73/1.06
(58) Field of Classification Search .............. 73/1.01, 73/1.02, 1.03, 1.06, 1.07
  See application file for complete search history.

(56) References Cited

U.S. PATENT DOCUMENTS

| | | | |
|---|---|---|---|
| 3,740,195 A | 6/1973 | Lietzau | |
| 4,116,336 A * | 9/1978 | Sorensen et al. | 206/524.8 |
| 4,268,478 A | 5/1981 | Huber | |
| 4,441,356 A | 4/1984 | Bohl | |
| 4,643,976 A * | 2/1987 | Hoskins | 436/15 |
| 4,960,708 A * | 10/1990 | Zowtiak et al. | 436/11 |
| 5,093,269 A | 3/1992 | Leichnitz et al. | |
| 5,096,669 A * | 3/1992 | Lauks et al. | 204/403.02 |
| 5,357,781 A | 10/1994 | Tikijian | |
| 5,374,400 A | 12/1994 | Sprinkle et al. | |
| 5,421,981 A * | 6/1995 | Leader et al. | 204/403.13 |
| 5,635,631 A | 6/1997 | Yesudas et al. | |
| 5,780,302 A * | 7/1998 | Conlon et al. | 436/8 |
| 6,451,606 B1 * | 9/2002 | Konig et al. | 436/8 |
| 6,475,158 B1 * | 11/2002 | Orr et al. | 600/531 |
| 6,588,250 B2 * | 7/2003 | Schell | 73/1.06 |
| 6,632,675 B1 * | 10/2003 | Conlon et al. | 436/11 |
| 6,835,571 B2 * | 12/2004 | Conlon et al. | 436/11 |
| 2002/0157447 A1 * | 10/2002 | Schell | 73/1.06 |
| 2005/0197596 A1 * | 9/2005 | Bellucci et al. | 600/573 |
| 2006/0219576 A1 * | 10/2006 | Jina | 205/792 |

(Continued)

FOREIGN PATENT DOCUMENTS

DE   10102820   7/2002

(Continued)

*Primary Examiner*—David A. Rogers
(74) *Attorney, Agent, or Firm*—Kris T. Fredrick

(57) ABSTRACT

A system for testing and calibrating gas sensors with gas stored in a strip of packets. The strip may be fed into a chamber having a defined volume of air. A packet may be punctured with a mechanism to release one or more gases into the volume of air to result in an air-gas mixture. New air may be moved into the chamber to push the mixture out of the chamber to a sensor for testing and/or calibration. Then another packet may be punctured to release one or more gases into the volume of new air in the chamber for another air-gas mixture. This mixture may be moved out of the chamber, in the same manner as the previous mixture, to another sensor for testing and/or calibration. This procedure may be repeated with additional packets on the strip.

16 Claims, 5 Drawing Sheets

U.S. PATENT DOCUMENTS

2006/0263254 A1* 11/2006 Lee .............................. 422/83
2008/0217246 A1* 9/2008 Benn et al. .................. 210/645
2008/0234562 A1* 9/2008 Jina ........................... 600/365
2008/0254494 A1* 10/2008 Heroux et al. ................ 435/23
2008/0254542 A1* 10/2008 Lunding ........................ 436/8

FOREIGN PATENT DOCUMENTS

WO          9004174      4/1990

* cited by examiner

GAS SENSOR TEST AND CALIBRATION SYSTEM

BACKGROUND

The invention relates to gas sensors, and particularly to testing and calibration of sensors.

SUMMARY

The invention is a mechanism that provides a stored amount of gas released into a defined volume of air. The gas and air mixture may be transported to a sensor for testing and/or calibration of the sensor.

DESCRIPTION

Figure 1:
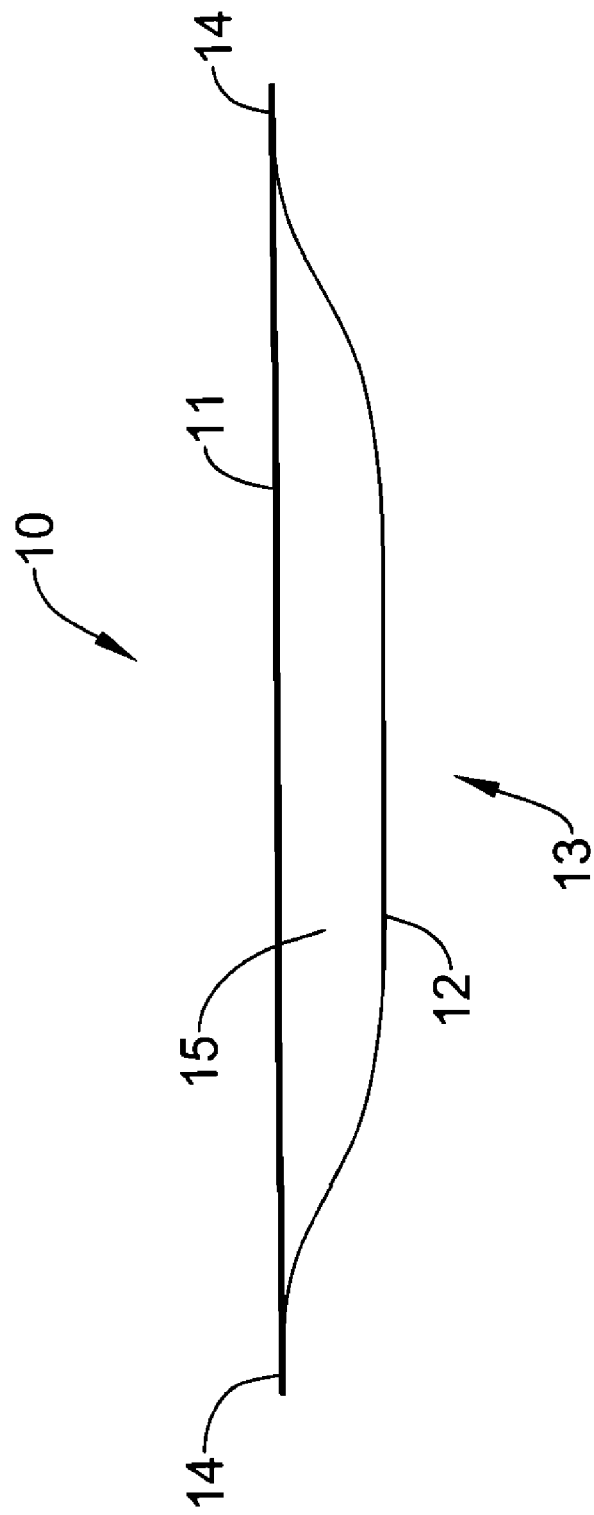
FIG. 1 is a diagram of a storage unit for holding a defined amount of gas for sensor testing.

Gas sensors should be functionally tested and calibrated periodically. In some places, functional testing and some calibration may be a requirement for sensors, for example, personnel sensor badges in a facility where a potential for a presence of a harmful gas exists.

A mechanism that is capable of providing multiple gases in one run for health determination and, in some instances, for calibration of one or more sensors is desired. The present invention may provide a mixture of test gases in air, and to check and also calibrate sensors for CO, $H_2S$, combustible gases, and other gases.

The gases of significant interest may include CO, $CH_4$, and $H_2S$. These three gases should not react with each other at ambient conditions. The three gases may be put together or mixed for incorporation and sealed inside of a blister pack. The pack may be made of low permeability plastics or their metalized derivatives. These blisters may be punctured open at one per run to test and calibrate a sensor module. A number of blister packs may be made and stored in the form of a strip and wound into a roll. Single blisters may be rolled off and punched or punctured open in a manner similar to a way that a cap gun pops small explosive-like and noisy caps. To assure reproducible gas pulses to the sensors, a release of the gases may be released into a fixed amount or volume of air. Then this volume of air, mixed with a determined or fixed amount of released gases, may be transported as a particular air-gas mixture to a gas sensitive area of one or more sensors.

Each single blister pack may be sealed or bonded with a cold working aluminum onto aluminum (for a good seal) or with an adhesive having a long diffusion length. A provision for transport of the gases to the sensors may also be provided.

A generation or providing of gases for checking gas sensors may be effected electrochemically, thermally, or in some other manner. An illustrative example here may include a bubble foil, blister, or similar enclosure for holding and providing the gas. Gas is not necessarily generated but may be stored in a form that makes a release of the gas easy and reproducible.

The present system may provide an alternative to gas generation. Current bump tests may be performed with a gas mixture from a tank (2.5 percent of $CH_4$, 100 ppm CO, 40 ppm $H_2S$, 15 percent of $O_2$). One may provide for a similar gas mixture from a small unit. To fill 1 mL of air with 1 percent of CH4, 100 ppm CO, and 40 ppm $H_2S$, one may need a volume of 10 uL of $CH_4$.

An approach of the present system may include the following items. First, one may make long band of bubble foil with bubbles of about 20 uL out of aluminized polymer like Mylar, and fill them with a gas mixture without overpressure. Second, one may roll the band of bubbles onto a cylinder and pull off one bubble at a time. Third, for each bump test, one may puncture one bubble with a "hammer", like a cap gun does when it generates a shooting sound from a roll, with chemicals. Fourth, one may let the gas mix with 2 mL of air in an enclosed volume, and pump air through the volume. Fifth, one may pump the gas mixture over the sensors.

A roll for 800 2 mL-pulses could have a width of about one inch and a diameter of about two inches, which does not seem prohibitively large for fixed sensors. Bubble foil appears to be the easiest approach for fixed sensors. This approach may be used for testing portable sensors such as those implemented in personal badges.

An alternative to gas generation may include some of the following items. FIG. 1 shows a blister pack or bubble foil 10. The bubble foil 10 may have bubbles 13 made out of aluminum foil 11 for a base and have aluminum or an aluminized polymer (e.g., Mylar) 12 for the bubble side. The aluminum foil 11 and the aluminum or aluminized polymer 12 may be joined and sealed by heat or ultrasound at a border 14 of the bubble to contain a gas 15. The bubble 13 may be filled with a desired gas or gases 15 before or after the sealing of the border 14. A design of the bubble or blister may be one among other approaches, packets or packages for keeping or storing gases until needed for testing and/or calibration of sensors.

Figure 2:
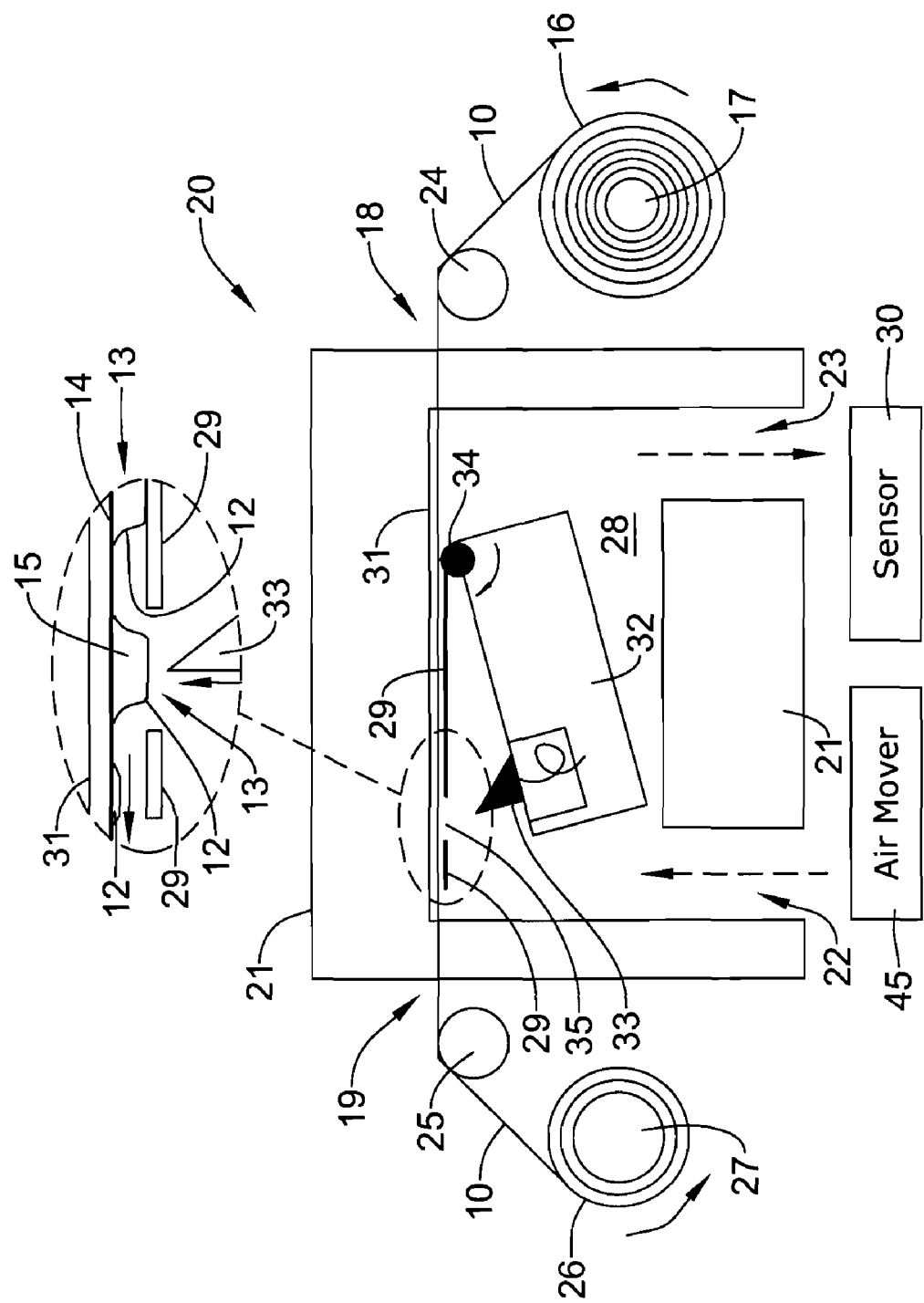
FIG. 2 is a diagram of an overall mechanism for gas sensor testing.

As indicated in FIG. 2, the foil 10 may be rolled up into a coil 16 and installed in a mechanism or source 20 on a coil or spool holder 17. The foil may be fed from coil 16 through a container 21 via slots 18 and 19, respectively. The slots 18 and 19 are such so as to provide somewhat air tight integrity to container 21 with the foil 10 moving through the slots. Roller 24 may guide the foil 10 through slot 18. Roller 25 may guide a punctured foil 10 out of slot 19 to be wound as a coil 26 on a wind-up spool 26. Container 21 may have an input port 22 and an output port 23 for air to enter and for a gas air mixture to exit, respectively.

For each bump test, one bubble 13 may be punctured and emptied into a defined volume 28 of container 21. There may be a plate 29 situated to keep foil 14 flat against an inside surface 31 of container 21. A device 32 may have a pointed object 33 attached and facing plate 29. Device 32 may be rotated about a hinge or anchor 34 towards the plate 29. During this rotation, pointed object 33 may puncture a bubble 13 formed by foil 12, or other material, by going through a hole 35 of plate 29 as the bubble passes by the hole. During this puncture of bubble 13, a certain or defined amount of a particular gas 15 may be released into the chamber 28. Upon the release of the gas, air may be pumped through port 22, for instance with an air mover 45, into the volume 28 and the certain or defined volume of air with the bubble 13 of gas 15 may be pushed out of volume 28 through port 23 to one or more gas sensors 30 to be tested (e.g., a health check) and/or calibrated.

Permeability and chemical resistance of the bubble 13 may be noted for preservation of the gas 15. For instance, an all-metal enclosure should keep $CH_4$ with traces of CO and $H_2S$ inside each bubble 13. A desired permeability of the material containing the bubble or blister 13 may about $10^{-15}/cm^2$. Aluminum may be reported to be stable in conjunction with $H_2S$. However, a question is whether the aluminum may deplete some of the $H_2S$. Depending on layout and circumstances of the setup and testing, the answer may be no. However, if the answer is assumed to be yes, $H_2S$ might be generated separately and/or provided outside of bubble 13. Or bubble 13 may be made with other materials. One may further note whether $H_2S$ is safe and compatible, and whether $H_2S$ is sufficiently inexpensive for use with the present system in testing and/or calibration of sensors. The answer may depend on an application of the system or source 20.

Figure 3:
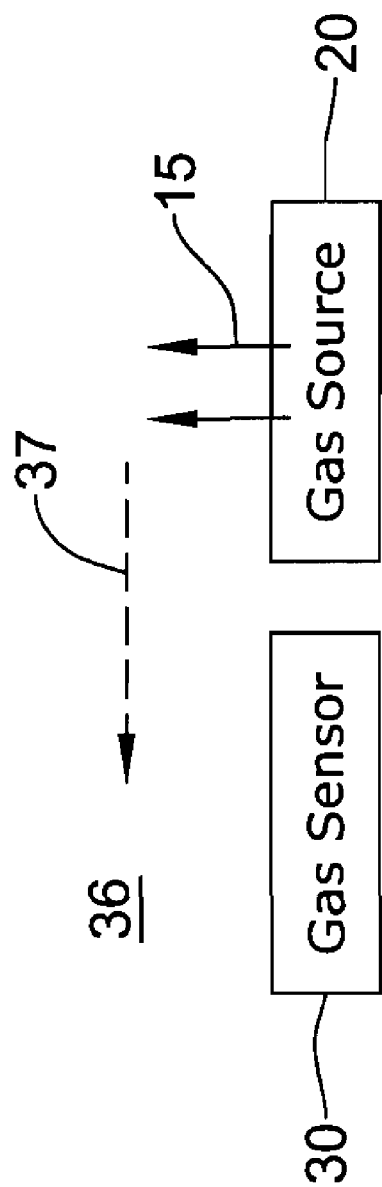
FIG. 3 is a diagram showing a gas transport from a source to a gas sensor.

A gas transport 37 from a gas source 20 to a sensor 30 may be noted in FIG. 3. Fixed and portable sensors may require different approaches. For fixed gas sensors, there may be transport of gases 15 through or from the ambient 36 to the sensor 30 by diffusion and/or convection. There may be some space available and full automatization may be desired. For portable gas sensors, transport of gases 15 from the ambient 36 to the sensor may often be effected by pumping. Space may be at a premium and human action possible or desirable for effecting transport.

Figure 4:
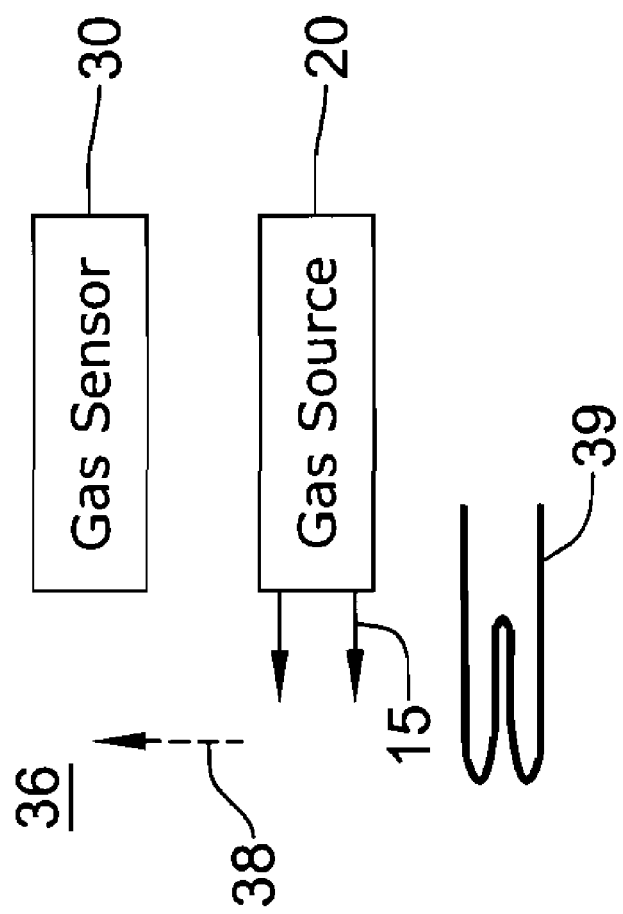
FIG. 4 is a diagram of a thermal transport for gas from a source to a gas sensor.

A flow design for fixed gas sensors might include reproducible gas pulses by an active transport, as diffusion may appear unacceptably slow and convection be unpredictable. Heat convection for gas transport 38 is shown by a diagram of a setup in FIG. 4. A heating element 39 may be placed proximate to the output port of gas source 20 to heat the gas 15 which will rise to follow the path of the gas transport 38 of the ambient 36. The gas 15 may eventually reach gas sensor 30 to be sensed. Heat convection appears easy but not necessarily optimal for reproducibility.

Figure 5:
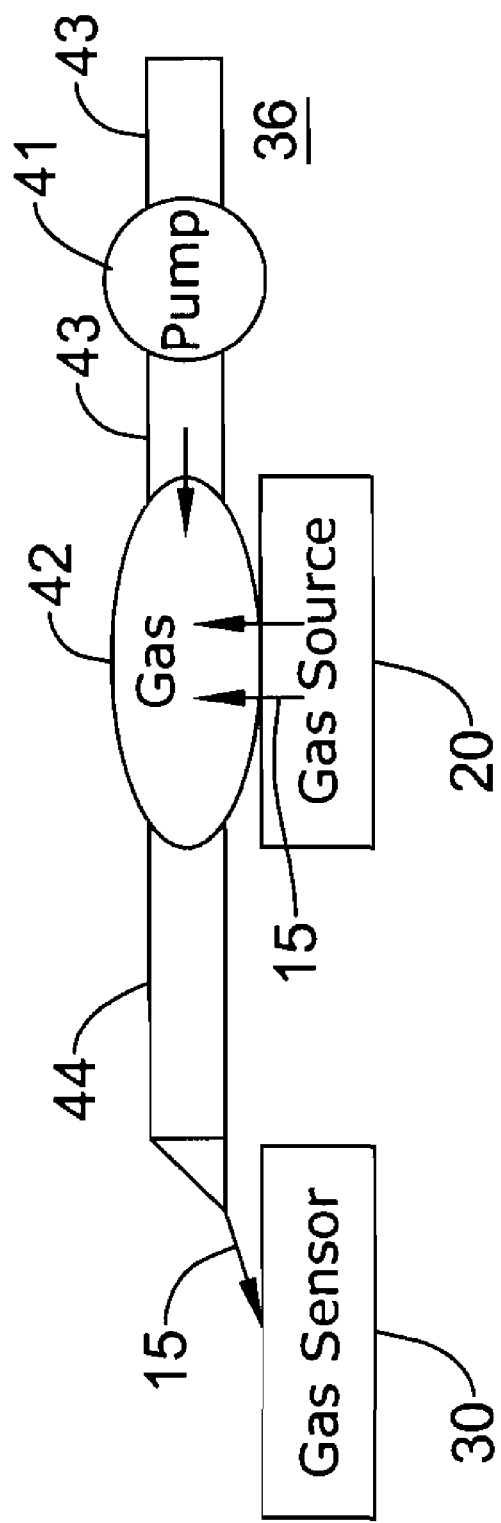
FIG. 5 is a diagram of an example pump transport for gas from a source to a gas sensor.

A pumping a gas pulse may result in the highest reproducibility for calibration. For example, a pump 41 may be included in a fixed gas sensor arrangement as shown in FIG. 5. Pump 41 may take air from the ambient 36 and push the air into a gas container 42 via a channel 43. Container 42 may be for receiving gas 15 from a gas source 20. Gas 15 may be pushed from container 42 by air from pump 41 through a channel 44 to a gas sensor 30 for detection. A fixed volume of air may be determined and pumped according to a volume or amount of gas released into container 42. The overall system with the pump may relax space requirements for a gas source 20 (which could fit in a flameproof housing for safety purposes). Further, the present pump system may be economical if the pump 41 is inexpensive. An example of such a pump may be a Mesopump™ produced in a 10,000 unit volume (by a company like Honeywell). A number of mesopump units may be connected together for increased capacity. A mesopump arrangement may have a capacity to provide 12 mL/min at about 40 uW. It may have a size of about 10×10×2 mm and operate at a temperature up to 100° C. The pump may provide a 3 kPa pressure difference or differential.

A flow design may be provided for portable gas sensors. The design may be more complex for portables than for fixed sensors. Reproducible gas pulses may be provided by an active transport in a portable design. It may be noted that dominant gases could include combustibles, $H_2S$, and the like. An existing pump 41 may be utilized for gas transport from a gas source 20. Or, one may let a manual operator press a button that drives pumping (which may be difficult in that the sensor or sensors should feel the gas). An integration of a source 20 may need a stronger interaction with the design of a sensor system. One may instead begin with fixed sensors rather than portable sensors, and make frequent visits to them unnecessary.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A test and calibration system comprising:
   a housing comprising:
      a chamber;
      a plurality of gas-filled packets; and
      an opener for releasing gas from a packet of the plurality of gas-filled packets, into the chamber; and
   wherein:
   the plurality of gas-filled packets is attached to a strip that goes into the chamber; and
   the strip is in a form of a roll on a spool which is fed into the chamber.

2. The system of claim 1, wherein:
   the chamber has a fixed amount of air;
   the packet has a fixed amount of gas; and
   the fixed amounts of gas and air become an air-gas mixture having a determined ratio of gas to air; and
   the determined ratio of gas to air is for testing and/or calibrating one or more sensors.

3. The system of claim 1, further comprising an air mover connected to the input port.

4. The system of claim 3, wherein:
   the air mover provides air into the chamber; and
   a releasing of gas from a packet provides gas to be mixed with the air in the chamber as an air-gas mixture.

5. The system of claim 4, wherein a gas sensor is tested with the air-gas mixture from the chamber.

6. The system of claim 5, wherein a testing of one or more gas sensors is on a one-to-one basis relative to each releasing of gas from a gas-filled packet of the plurality of gas-filled packets.

7. A method for testing sensors comprising:
   providing a plurality of blister packs wherein each blister pack contains one or more gases;
   releasing the one or more gases from a blister pack in a chamber having air resulting in an air-gas mixture in the chamber; and
   moving the air-gas mixture from the chamber to a sensor for testing and/or calibration of the sensor; and
   wherein:
   the plurality of blister packs is on a strip feed-able into the chamber; and
   the strip is in a form of a roll on a spool which is fed into the chamber.

8. The method of claim 7, wherein the releasing of one or more gases of specific amounts from a blister pack and a mixing of the one or more gases with a specific amount of air provides an air-gas mixture sufficient for testing and/or calibration of one sensor.

9. The method of claim 7, wherein the releasing of one or more gases is effected by a mechanism which punctures a blister pack.

10. The method of claim 7, wherein one or more sensors are tested per releasing the one or more gases from a blister pack.

11. The method of claim 10, wherein:
the releasing of one or more gases from N blister packs individually into N first quantities of air is for tests and/or calibrations of N sensors; and
N is a positive integer.

12. A system for test and calibration comprising:
a plurality of packages containing one or more gases;
a chamber having a defined volume; and
a mechanism for releasing a defined amount of one or more gases from a package of the plurality of packages into the defined volume; and
wherein:
the chamber has an output port for providing an air-gas mixture;
the plurality of packages is situated on a strip which is fed into the chamber to the mechanism for a releasing of the defined amount of one or more gases from a package; and
the strip is in a form of a roll on a spool which is fed into the chamber.

13. The system of claim 12, further comprising:
an air mover connected to an input port of the chamber; and
wherein the air mover provides a volume of air approximately equivalent to the defined volume for mixture with the defined amount of one or more gases released from a package of the plurality of packages to result in an air-gas mixture.

14. The system of claim 13, wherein the air-gas mixture is for testing and/or calibrating at least one gas sensor.

15. The system of claim 14, wherein each air-gas mixture includes one package of one or more gases and the air in the chamber.

16. The system of claim 15, wherein each package is a blister pack which has an aluminum base with aluminum or an aluminized polymer formed like a bubble, including space for the one or more gases, having a border sealed to the aluminum base.

* * * * *